(12) United States Patent
Richter et al.

(10) Patent No.: US 10,386,350 B2
(45) Date of Patent: Aug. 20, 2019

(54) MOBILE DEVICE FOR DETERMINING A COMPONENT IN AMBIENT AIR

(71) Applicant: Fraunhofer-Gesellschaft zur Foerderung der angewandten Forschung e.V., Munich (DE)

(72) Inventors: Martin Richter, Munich (DE); Christoph Jenke, Munich (DE); Siegfried Roehl, Sauerlach (DE); Christoph Kutter, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 67 days.

(21) Appl. No.: 15/435,765

(22) Filed: Feb. 17, 2017

(65) Prior Publication Data
US 2017/0241963 A1 Aug. 24, 2017

(30) Foreign Application Priority Data
Feb. 19, 2016 (DE) .................. 10 2016 202 609

(51) Int. Cl.
*G01N 33/00* (2006.01)

(52) U.S. Cl.
CPC ..... *G01N 33/0031* (2013.01); *G01N 33/0036* (2013.01); *H04M 2250/12* (2013.01)

(58) Field of Classification Search
CPC .......... G01N 33/0004; G01N 33/0009; G01N 33/497; G01N 33/4972; H04M 2250/12; H04M 1/026
See application file for complete search history.

(56) References Cited

U.S. PATENT DOCUMENTS

| | | | | |
|---|---|---|---|---|
| 7,051,577 | B2 * | 5/2006 | Komninos | G01M 3/24 73/40.5 A |
| 9,021,866 | B2 * | 5/2015 | Takano | G01M 3/16 73/40.5 R |
| 9,739,762 | B2 * | 8/2017 | Schmidlin | G01N 33/0062 |
| 10,009,448 | B2 * | 6/2018 | Han | H04M 1/0202 |
| 2013/0276517 | A1 * | 10/2013 | Takano | G01M 3/16 73/40.5 R |
| 2014/0076022 | A1 * | 3/2014 | Ohlsson | G01N 33/4972 73/23.3 |
| 2014/0134053 | A1 | 5/2014 | Mayer et al. | |
| 2014/0216129 | A1 * | 8/2014 | Schmidlin | G01N 33/0062 73/23.2 |

(Continued)

FOREIGN PATENT DOCUMENTS

| | | |
|---|---|---|
| WO | 2015104221 A1 | 7/2015 |
| WO | 2016094007 A1 | 6/2016 |

*Primary Examiner* — David A Rogers
(74) *Attorney, Agent, or Firm* — Perkins Coie LLP; Michael A. Glenn (57) ABSTRACT

A mobile device includes an opening defining a fluid connection between a fluid channel in the mobile device and ambient air, and a sensor arranged in the fluid channel, configured to sense at least one component of the ambient air. The mobile device further includes a micropump configured to draw in the ambient air through the opening and to convey the same to the sensor. According to the invention, the sensor is arranged spaced apart from the opening, and the volume of the fluid channel between the sensor and the opening is less than 200 microliters.

12 Claims, 10 Drawing Sheets

(56) References Cited

U.S. PATENT DOCUMENTS

| | | | |
|---|---|---|---|
| 2014/0223995 A1* | 8/2014 | Buhler | G01N 33/0062 |
| | | | 73/29.02 |
| 2014/0225738 A1* | 8/2014 | Lechner | G08B 21/12 |
| | | | 340/603 |
| 2014/0238100 A1* | 8/2014 | Londergan | G01N 33/0006 |
| | | | 73/1.03 |
| 2015/0219608 A1* | 8/2015 | Choi | G01N 33/0004 |
| | | | 73/23.2 |

* cited by examiner

MOBILE DEVICE FOR DETERMINING A COMPONENT IN AMBIENT AIR

CROSS-REFERENCE TO RELATED APPLICATIONS

This application claims priority from German Patent Application No. 102016202609.7, which was filed on Feb. 19, 2016, and is incorporated herein in its entirety by reference.

The invention relates to a mobile device comprising the features of claim 1.

BACKGROUND OF THE INVENTION

Nowadays, more and more sensors are used. Many of these sensors measure environmental parameters such as $CO_2$, moisture, temperature or smoke. However, these sensors naturally do not measure the parameters of the room but the parameters within the respective device into which they are integrated. Then, an attempt is made to approximately extrapolate the parameters of the room air from the measuring signal of the sensor by means of complicated algorithms, which only partially succeeds.

Detection of gases such as CO, $N_2O$ or VOC as well as of water contents and the gas composition in our surroundings is in the interest of many people.

In addition, most people would like to instantly sense air polluting gases, fine dust and allergenic particles such as pollen at their location or receive early warnings of allergenic substances and hazardous gases. Moreover, the detection of odors such as breath alcohol, bad breath and many other odors is of interest.

Sensors are available for many of the applications mentioned. Although many of the available sensors (e.g., for humidity, volatile organic compounds VOC, CO or NO) or the sensors based on organometallic, optical or resonance principles comprise form factors and an appropriate cost-efficiency for use with portable devices, the commercial use is only possible in a limited extent, since the gas, the odor or the fine dust may not be delivered quickly and reliably to the sensor in a portable device in all sensor principles.

However, this is necessitated in order to provide the user with a meaningful and fast measurement result. Reliable data for gas measurements may provide meaningful gas overviews of the surroundings, e.g., air pollution along streets or in large cities, respectively, or pollen maps for people suffering from allergy.

In some cases, sensors are installed in bulky, stand-alone units. In some cases, mouthpieces have to be used with these devices, which many people do not like. An additional problem is that stand-alone devices with sensors necessitate display and computing capabilities, which incurs additional costs.

Such a specialized portable gas measuring device is known from WO 2015/104221 A1. The Reference refers to a sensor unit for a gas measuring device for detecting a gas. The transportable gas measuring device serves to monitor gases and vapors, in particular toxic gases in industrial environments. In general, it is about the change in a physical-chemical property of the receptor interacting with analyte molecules at the molecular level. In this connection, WO 2015/104221 A1 describes a combination of a pressure-tight measuring channel, a gas inlet, a gas outlet, a pump unit for evacuation, a gas sensor, a heating unit for the gas sensor and a sensor unit with a regeneration mode and a measuring mode.

As mentioned at the outset, the gas measuring device known from WO 2015/104221 A1 is a specialized apparatus intended exclusively for measuring gases in the ambient air. Such apparatuses provide good and reliable measurement results. However, such apparatuses necessitate a certain amount of time during which the gas sensor technology calibrates itself to provide a sufficiently reliable result. Such known devices are therefore not immediately ready for use, especially in cases where the conditions of the surroundings rapidly change. For example, this is the case when the device is moved from an outside area into an inside area such as a living room. In this case, known apparatuses necessitate a certain amount of time to "acclimatize", so to speak, which may be up to several minutes.

However, fast response times of the gas sensors are desirable for many applications of portable electronic devices, e.g., in the case of a rapid sensing of people by means of gas sensors, in the case of fire detection sensors or to sense when a person is entering a building. When taking this knowledge into account, the manufacturers of gas measuring devices would have to mount their sensors directly onto the housing surface in order to obtain a rapid signal. However, this is uneconomical or unfavorable for several reasons.

On the one hand, arranging the sensor on one of the circuit boards in the housing increases the assembly requirements and, inevitably, the associated assembly costs. In addition, if mounted directly onto the housing surface, there is the risk of damage to the sensor by external influences. On the other hand, if the sensor is installed on the outside of the gas measuring device, the housing may no longer be smooth. Moreover, if many gas sensors and other components (e.g., circuit boards, displays, etc.) are to be mounted close to the air inlet of the gas measuring device, there may not be enough space available.

SUMMARY

According to an embodiment, a mobile device may have: an opening defining a fluid connection between a fluid channel in the mobile device and ambient air, a sensor arranged in the fluid channel, configured to sense at least one component of the ambient air, a micropump configured to draw in ambient air through the opening and to convey the same to the sensor, wherein the sensor is arranged spaced apart from the opening, and the volume of the fluid channel between the sensor and the opening is less than 20 microliters and the length of the fluid channel between the sensor and the opening is less than 25 mm, advantageously less than 15 mm and more advantageously 10 mm or less.

Accordingly, a mobile device is proposed, comprising an opening defining a fluid connection between a fluid channel in the mobile device and ambient air. Furthermore, the mobile device comprises, arranged in the fluid channel, a sensor configured to sense at least one component of the ambient air. The mobile device also comprises a micropump configured to draw in ambient air through the opening and convey the same to the sensor, the sensor being arranged spaced apart from the opening. According to the invention, the volume of the fluid channel between the sensor and the opening is less than 200 microliters. By the micropump, diffusion of the ambient air used in conventional devices up to now is replaced with convection. As a result, the ambient air may enter the mobile device much more quickly and may be directed to the sensor through the fluid channel. In this connection, it has been found to be advantageous to design the fluid channel such that its volume is less than 200 microliters. Accordingly, approx. 200 microliters of the ambient air are in the fluid channel between the opening and the sensor. Micropumps are suitable to supply such volumes quickly and almost without losses. Thus, by means of the micropump, the ambient air may be drawn in and quickly be transported to the sensor.

Generally, the time necessitated for the drawn-in ambient air to reach the sensor may be significantly reduced compared to known, diffusion-based devices. While known devices generally necessitate several seconds up to a few minutes in order to be able to analyze the ambient air, the mobile device according to the invention may begin sensing a component in the ambient air after just a few seconds and in some cases within a few microseconds. Thus, by drawing in the ambient air by means of the micropump, the time necessitated to transport the drawn-in ambient air from the opening of the mobile device to the sensor through the fluid channel is significantly reduced. Hence, the ambient air to be analyzed is supplied to the sensor as quickly as possible. Therefore, the sensor may sense within the shortest time at least one component or, advantageously, several components in the ambient air so as to analyze the ambient air. For example, with the present invention, a user of a mobile device such as a smartphone may quickly be made aware of a smoke development in the surroundings in order to warn the user of an erupting fire as early as possible.

According to an embodiment, the volume of the fluid channel between the sensor and the opening may be less than 20 microliters. A volume of less than 20 microliters may be quickly moved and/or supplied even by micropumps of very small dimensions, e.g., micropumps produced in a Si-chip design. As a result, the time necessitated to transport the drawn-in ambient air from the opening of the mobile device to the sensor is advantageously reduced.

It is conceivable that the mobile device is a mobile telephone and the opening provided in the mobile telephone is a microphone opening. Nowadays, mobile telephones are widespread and available in numerous implementations. Usually, the housing of a mobile telephone comprises an opening behind which there is a microphone. This already existing microphone opening may advantageously be used in the present invention as an opening for drawing in the ambient air.

According to an embodiment, the distance between the sensor and the opening may be less than 25 mm, advantageously less than 15 mm, and more advantageously 10 mm or less. In order to keep the transport paths of the drawn-in ambient air in the fluid channel as short as possible, the sensor should be arranged as close to the opening as possible. For structural reasons, i.e, for reasons of space with regard to packaging, the sensor may not always be placed directly at the opening, but may be arranged spaced apart from the opening. In this connection, it has been found to be particularly advantageous to adjust the distance between the sensor and the opening within the abovementioned ranges. Thus, a sufficiently fast transport of the drawn-in ambient air from the opening to the sensor may be ensured.

According to an embodiment, the distance between the sensor and the opening may be at least 5 mm. As already mentioned, for reasons of space, it may be necessitated to arrange the sensor to be spaced apart from the opening. Apart from this, when mounting the sensor directly at the inside of the housing, i.e., directly at the opening, the risk of damage to the sensor by an action from the outside rises. It has been found that a spacing of approx. 5 mm between the sensor and the opening provides a good protection of the sensor on the inside of the housing.

It is conceivable that the micropump comprises a lateral dimension of 5×5 mm or less and a height of 1 mm or less. Such miniaturized micropumps are particularly suitable to be housed in a mobile device in a space-efficient manner. Moreover, such micropumps may be manufactured simply, i.e., inexpensively, e.g., in the form of semiconductor chips such as Si-microchip pumps.

It is further conceivable that the sensor comprises a lateral dimension of 1.5×1.5 mm or less and a height of 1 mm or less. Such miniaturized sensors are particularly suitable to be housed in a mobile device in a space-efficient manner.

According to an embodiment, the mobile device may comprise a sensor array comprising at least the one sensor and at least one further sensor for sensing a component of the ambient air. Advantageously, the sensor array may comprise a total of up to twenty sensors for sensing a component of the ambient air. Such a sensor array may comprise a larger size of up to, e.g., 5 mm×30 mm. A sensor array may comprise several sensors which may measure either the same component in the ambient air or different components in the ambient air. With such an array with several sensors, the time for sensing several components in the ambient air may be significantly reduced. On the other hand, e.g., in the case of at least two sensors which, if applicable, may both sense the same component in the ambient air, one of the two sensors may be configured as a calibration sensor. That is, while one sensor senses the unfiltered ambient air, the other sensor may circumflowed by filtered ambient air for a comparison and/or calibration, or also by calibration gases.

In an embodiment, the micropump may be arranged upstream of the sensor. In this case, the micropump comprises at least one inlet and one outlet. In this case, the micropump is, so to speak, connected between the opening and the sensor. The micropump draws in ambient air through its inlet and pumps the same to the sensor arranged downstream through its outlet. In this connection, the paths between the pump and the opening in the housing may be kept short.

In a further embodiment, the micropump may be arranged downstream of the sensor. This offers the advantage that the drawn-in ambient air does not have to be pumped through the micropump. Thus, the ambient air hits the sensor directly after entering through the opening in the housing. In this way, flow losses may be kept low since the drawn-in air does not have to take the detour through the micropump and the drawn-in ambient air may be guided onto the sensor in an unfiltered manner, if necessitated.

It is conceivable that the mobile device further comprises a filter, in particular an activated carbon filter, a hydrophobic filter, a hydrostatically charged filter or a Teflon filter. For example, such filters may be used to prevent the entry of larger particles such as dust particles. However, it is also conceivable that, e.g., activated carbon filters are used in order to substantially clean the ambient air and, thus, to provide a "reference ambient air". The same may, for example, be used for calibrating the sensor. Activated carbon filters may also be advantageously used in a mobile device according to the invention in order to, e.g., clean the ambient air from the molecules or particles which are to be measured by the sensor or against which the sensor exhibits a cross-sensitivity. Hydrophobic filters may be used to separate moisture from the ambient air if humidity is not desired when measuring by means of the sensor.

In an embodiment, the mobile device may comprise a second fluid channel configured to transport drawn-in ambient air to the sensor, and a filter may be arranged in the second fluid channel. Thus, for example, the first sensor may measure the unfiltered ambient air. The second sensor, on the other hand, may measure filtered ambient air as a reference.

In this case, it is conceivable that the mobile device comprises a second micropump configured to draw in the ambient air and to transport it to the sensor through the second fluid channel. The two micropumps may be operated independently of one another. Thus, the fluid channels may also transport drawn-in ambient air to the respective sensors independently of one another.

According to an embodiment, the sensor may be configured to sense at least one ambient air component from the group consisting of carbon monoxide (CO), carbon dioxide ($CO_2$), nitrogen (N), dinitrogen monoxide ($N_2O$), volatile organic compounds (VOC), humidity, allergenic substances and fine dust. It is also conceivable that the sensor may sense non-toxic gases or even toxic gases in a non-toxic range. It would also be conceivable that the sensor may measure other phases such as liquids or solids in the air. Thus, for example, advantageously moisture or even fine dust could be sensed in the ambient air.

According to an embodiment, the sensor may be a sensor without need of regeneration. In other words, the sensor may function approximately consistently well without having to be regenerated. Sensors without need of regeneration do not cause a physical-chemical change at the sensor membrane. This shortens the response time and prolongs the service life of the sensor. Known sensors have to go through a regeneration process in which the sensor membrane is heated in order to release the parts adhering to the sensor membrane. However, multiple heating operations may reduce the service life of the sensor.

It is conceivable that the mobile device is a bracelet, a watch, a tablet or a notebook. Nowadays, such mobile devices are widespread and often carried by users. The existing hardware such as processors, memories, displays, etc. may be used to operate the micropump as well as the sensor, and to appropriately evaluate the sensor data.

BRIEF DESCRIPTION OF THE DRAWINGS

Embodiments of the present invention will be detailed subsequently referring to the appended drawings, in which.

DETAILED DESCRIPTION OF THE INVENTION

Identical parts shown in the figures comprise the same reference signs. In the following description of the figures, the structural features of embodiments of the mobile device according to the invention will be described first. Subsequently, the function of the mobile device 1 according to the invention will be explained in more detail.

Figure 1:
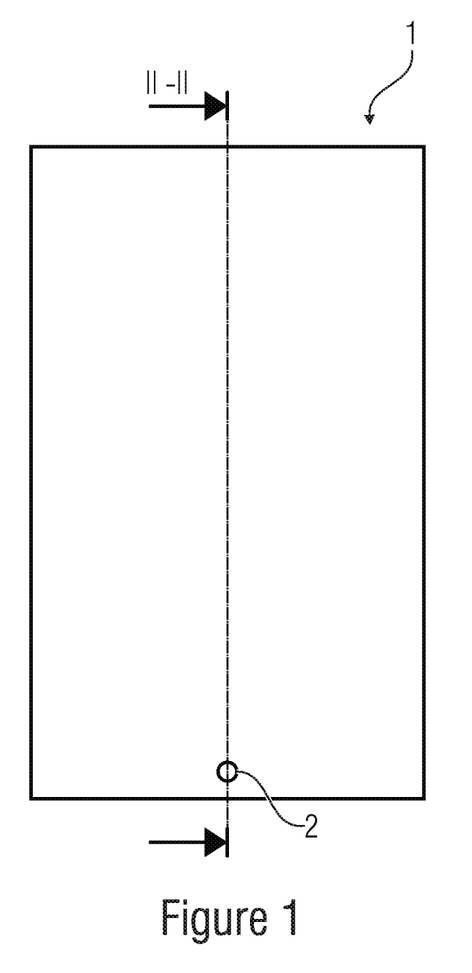
FIG. 1 is a top view of a mobile device according to the invention.

FIG. 1 exemplarily shows a mobile device 1 in a top view. The mobile device 1 comprises an opening 2.

Figure 2:
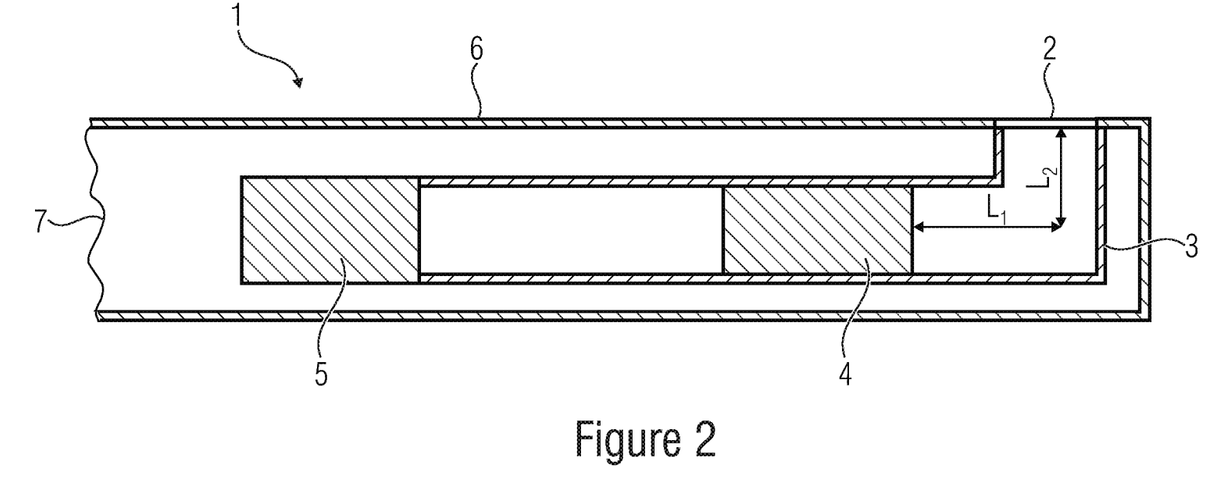
FIG. 2 is a schematic sectional view along the sectional line II-II shown in FIG. 1.

FIG. 2 shows an enlarged sectional view of the mobile device 1 along the sectional line II-II depicted in FIG. 1. Since the mobile device 1 is illustrated enlarged in FIG. 2, FIG. 2 only shows a section of the mobile device 1 in which the opening 2 is located. An interruption line 7 indicates that the mobile device 1 may extend further laterally.

The mobile device 1 comprises an opening 2. The opening 2 defines a fluid connection between a fluid channel 3 in the mobile device 1 and ambient air. Ambient air is the air that is located in the surroundings, i.e., outside of the mobile device 1.

A sensor 4 is arranged in the fluid channel 3. The sensor 4 is configured to at least sense one component of the ambient air.

The mobile device 1 further comprises a micropump 5. The micropump 5 is configured to draw in the ambient air through the opening 2 and convey the same to the sensor 4.

As may be seen in FIG. 2, the sensor 4 is arranged spaced apart from the opening 2.

At least a part of the fluid channel 3 extends between the opening 2 and the sensor 4 arranged spaced apart therefrom. The volume of the fluid channel 3 between the sensor 4 and the opening 2 is less than 200 microliters.

According to an embodiment, the volume of the fluid channel 3 between the sensor 4 and the opening 2 is less than 20 microliters.

In the embodiment shown in FIG. 2, the depicted mobile device 1 is a mobile telephone or a mobile radio device. The mobile telephone 1 comprises a housing 6. The opening 2 is provided in the housing 6. In this case, the opening 2 is the microphone opening of the mobile telephone 1. It would be conceivable that a microphone (not depicted herein) is arranged in the fluid channel 3, between the opening 2 and the sensor 4.

In the embodiment depicted in FIG. 2, the length L of the fluid channel 3 between the sensor 4 and the opening 2 is less than 25 mm. More specifically, the length L of the fluid channel 3 is composed of a first portion $L_1$ and a second portion $L_2$. In the embodiment depicted in FIG. 2, the fluid channel 3 extends horizontally with the length $L_1$ and vertically with the length $L_2$ within the mobile device 1.

Figure 3:
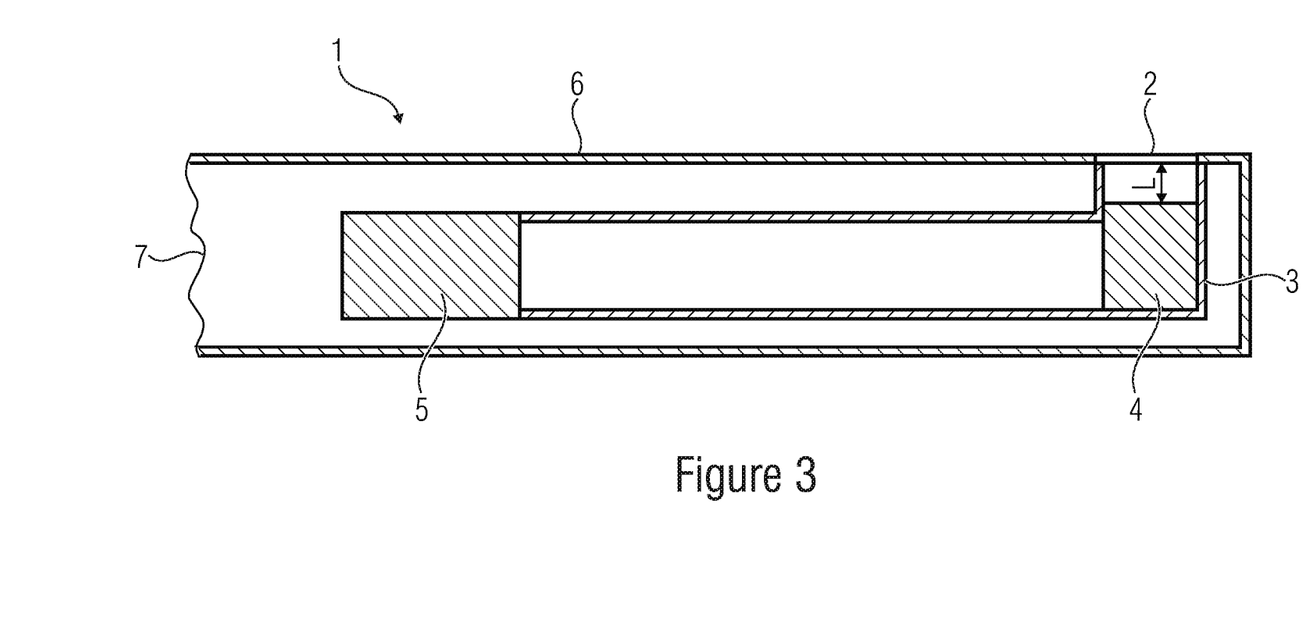
FIG. 3 is a sectional view of a further schematically illustrated embodiment of a mobile device according to the invention.

FIG. 3 shows a further possible embodiment. Here, the sensor 4 is arranged closer to the opening 2. More specifically, the sensor 4 is arranged in the fluid channel 3 such that the distance L between the sensor 4 and the opening 2 is less than 10 mm. In other words, the length L of the fluid channel 3 between the opening 2 and the sensor 4 is less than 10 mm.

However, the sensor 4 is arranged spaced apart by more than 5 mm from the opening 2. In other words, the length L of the fluid channel 3 between the sensor 4 and the opening 2 is at least 5 mm. As mentioned above, it is generally not always possible to provide the sensor 4 directly adjacent to the opening 2.

Figure 4:
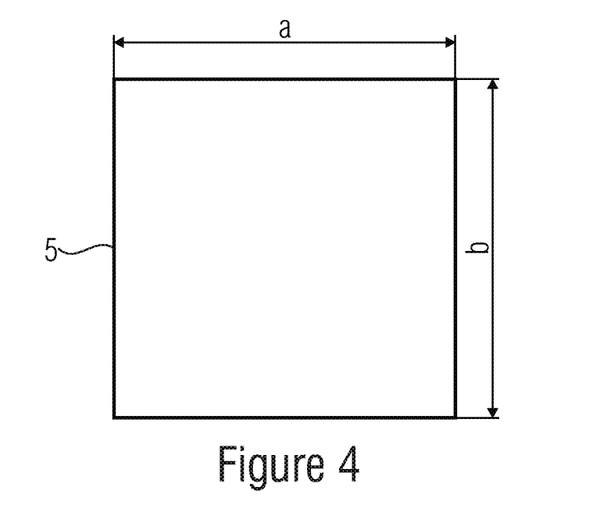
FIG. 4 is a top view of a schematically illustrated micropump.

FIG. 4 shows a top view of a micropump 5. The micropump 5 comprises lateral dimensions of 5×5 mm or less. That is, the side lengths a, b are of a length of at most 5 mm. In the embodiment depicted in FIG. 4, the side lengths a, b are of the same length so that the micropump 5 comprises a square shape. However, the side lengths a, b may also be of different lengths so that the micropump 5 comprises a rectangular shape.

The same applies to the sensor 4. In an embodiment, the sensor 4 comprises a lateral dimension of 1.5×1.5 mm, i.e., the side lengths a, b are each of a length of 1.5 mm.

Figure 5:
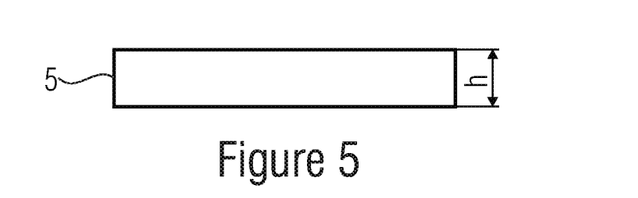
FIG. 5 is a side view of a schematically illustrated micropump.

FIG. 5 shows a side view of a micropump 5. As may be seen, the micropump 5 comprises a height h. The height h is 1 mm or less. The sensor 4 may also comprise a height h of 1 mm or less.

Figure 6:
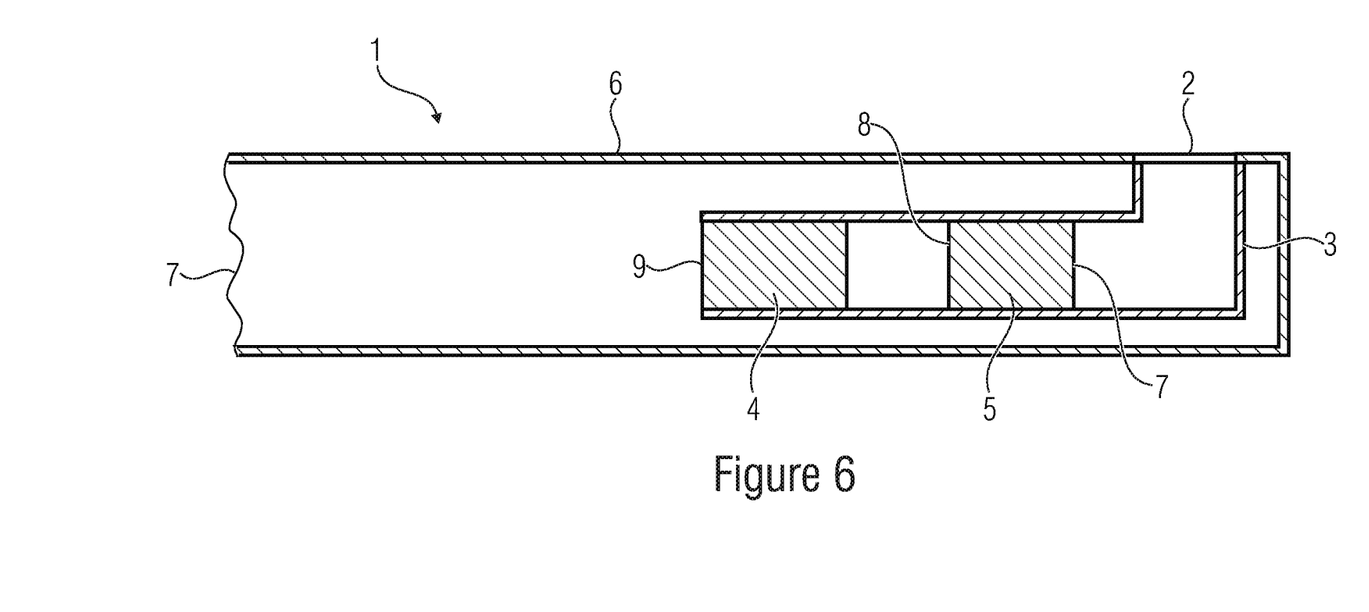
FIG. 6 is a sectional view of a further schematically illustrated embodiment of a mobile device according to the invention.

In the embodiments depicted in FIGS. 2 and 3, the micropump 5 was arranged downstream of the sensor 4. FIG. 6 shows a further embodiment in which the micropump 5 is arranged upstream of the sensor 4. Since the micropump 5 draws in the ambient air through the opening 2, the flow direction is the direction in which the drawn-in ambient air flows in the fluid channel 3. In this case, the drawn-in ambient air flows from the opening 2 in the direction of the micropump 5 drawing in.

The micropump 5 comprises an inlet 7 and an outlet 8. The sensor 4 is arranged at the end 9 of the fluid channel 3. The end 9 may be closed so that the sensor 4 is completely enclosed in the fluid channel 3. However, the end 9 may also be an open end 9, i.e., the end of the fluid channel 3 is not closed and the drawn-in ambient air flowing past the sensor 4 or flowing through the sensor 4 may escape from the open end 9 of the fluid channel 3.

Figure 7:
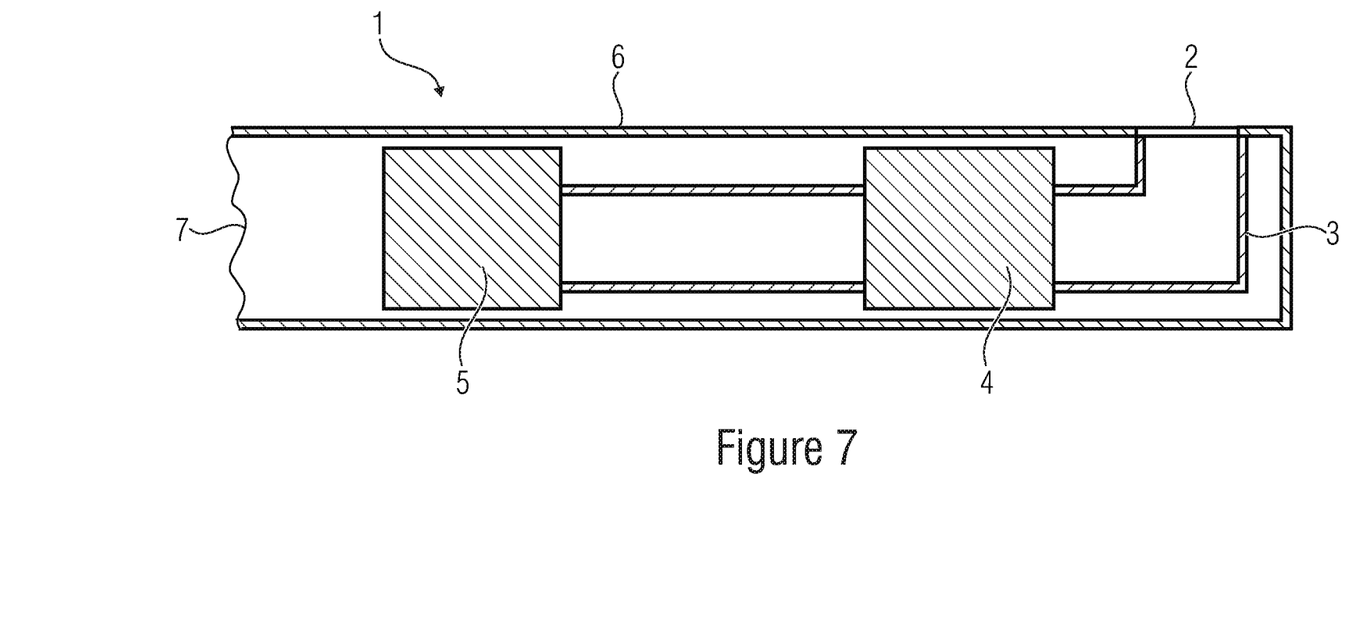
FIG. 7 is a sectional view of a further schematically illustrated embodiment of a mobile device according to the invention.

In the previously shown embodiments, the sensor 4 and the micropump 5 were arranged within the fluid channel, the outer dimensions of the sensor 4 or of the micropump 5 approximately corresponding to the diameter of the fluid channel 3. FIG. 7 shows a further embodiment. In this case, the outer dimensions of the sensor 4 or of the micropump 5 are larger as compared to the diameter of the fluid channel 3. In this case, the drawn-in ambient air flows through the sensor 4.

It is conceivable that the fluid channel 3 is configured in the form of one or several fluid lines interconnecting the opening 2, the sensor 4 and the micropump 5. The fluid lines may comprise a cross-section and/or a diameter which is smaller compared to the outer dimensions of the sensor 4 or the micropump 5, respectively, as depicted in FIG. 7.

Figure 8:
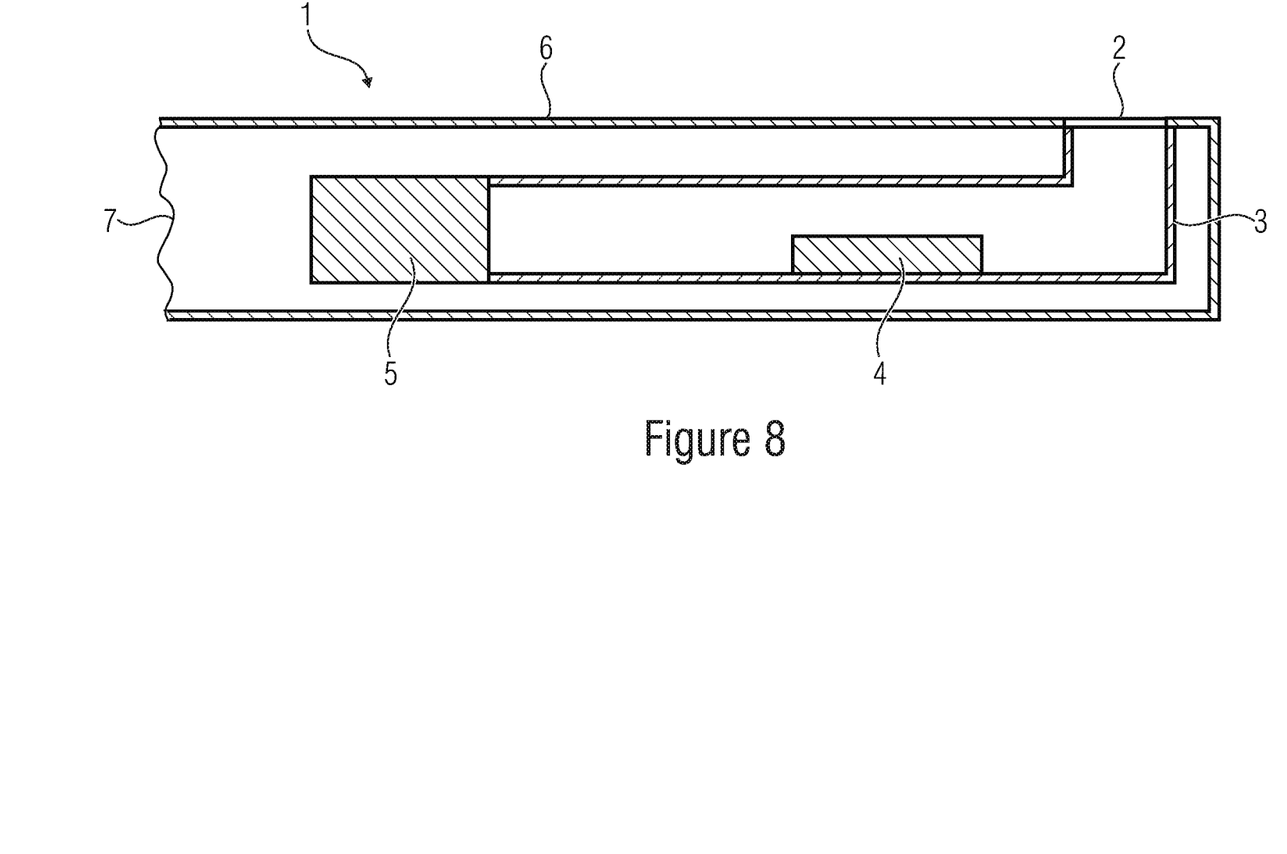
FIG. 8 is a sectional view of a further schematically illustrated embodiment of a mobile device according to the invention.

FIG. 8 shows a further embodiment. Here, the sensor 4 comprises at least a height h which is less than the cross-section and/or the diameter of the fluid channel 3. In this case, the drawn-in ambient air flows over the sensor 4. The micropump 5 may also comprise an outer dimension that is smaller than the cross-section and/or the diameter of the fluid channel 3 so that the micropump 5 is arranged within the fluid channel 3.

A combination of the embodiments of the components shown in FIGS. 6 and 7, in particular of the sensor 4 and the micropump 5, is also conceivable.

Figure 9:
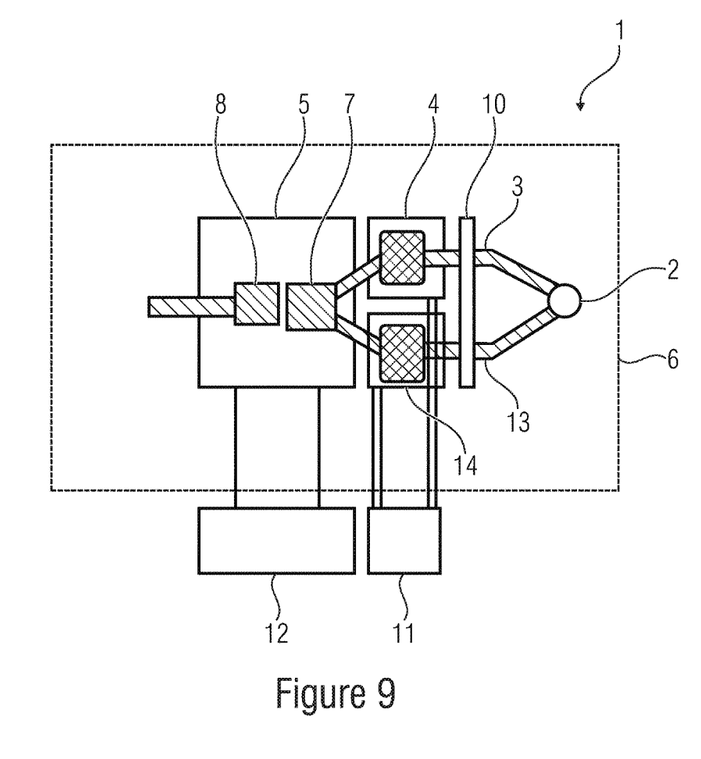
FIG. 9 is a top view of a further schematically illustrated embodiment of a mobile device according to the invention.

FIG. 9 shows a further embodiment of an apparatus 1 according to the invention in a schematic top view. The housing 6 of the mobile device 1 is indicated in dashed lines.

FIG. 9 shows a micropump 5 comprising an inlet 7 and an outlet 8, and a first sensor 4 and a second sensor 14. The first sensor 4 is arranged in a first fluid channel 3. The second sensor 14 is arranged in a second fluid channel 13. Both fluid channels 3, 13 extend to the inlet 7 of the micropump 5.

A filter element 10 is arranged upstream of the two sensors 4, 14 in at least one of the two fluid channels 3, 13. The filter element 10 may be an activated carbon filter, a hydrophobic filter or a Teflon filter.

The filter element 10 may be arranged both in the first fluid channel 3 and in the second fluid channel 13, as depicted in FIG. 9. However, it is also conceivable that a separate filter element is arranged in each of the first fluid channel 3 and the second fluid channel 13. In an embodiment, a filter element is arranged only in the second fluid channel 13. As described in more detail below, this may be used, e.g., for calibrating the sensor 4.

Moreover, the opening 2 provided in the mobile device 1 is located upstream of the two sensors 4, 14. The two fluid channels 3, 13 are connected to the opening 2 in order to provide a fluid connection between the mobile device 1 and the ambient air.

Moreover, the mobile device 1 comprises a pump control unit 12 as well as a sensor control unit 11. For example, these may be suitable microcontrollers. In the case that the mobile device 1 is a mobile telephone, a processor present in the mobile telephone 1 may take over the tasks of the pump control unit 12 or the sensor control unit 11, respectively.

Figure 10:
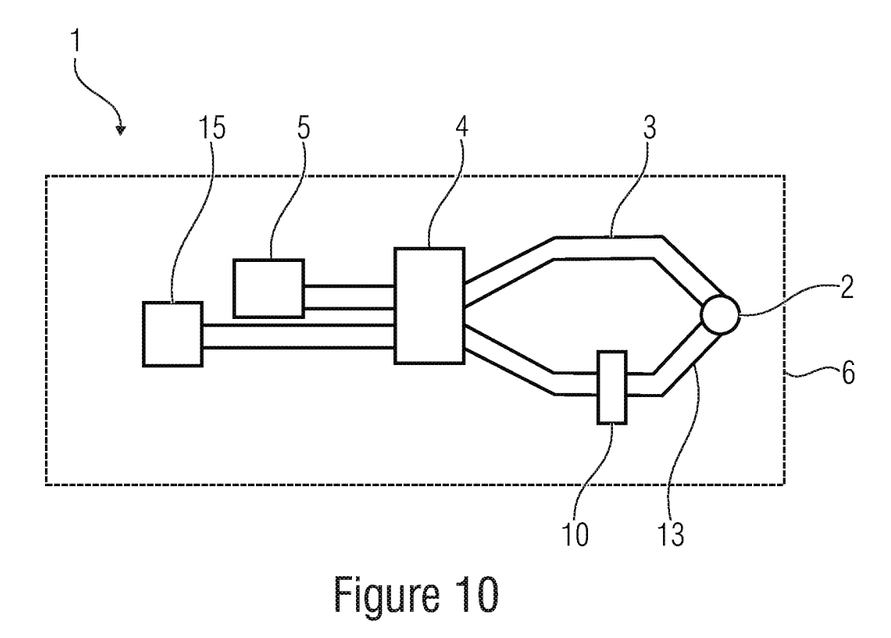
FIG. 10 is a top view of a further schematically illustrated embodiment of a mobile device according to the invention.

FIG. 10 shows a further schematic top view of an apparatus 1 according to the invention. Again, the housing 6 of the mobile device is schematically indicated in dashed lines.

A first fluid channel 3 and a second fluid channel 13 are arranged between the opening 2 and the sensor 4. A filter element 10 is arranged in the second fluid channel 13 between the sensor 4 and the opening 2.

In this embodiment, it would also be conceivable that two micropumps 5, 15 are provided. The first micropump 5 is configured to supply, upon operation, the ambient air to the sensor 4. The second micropump 15 is configured to supply, upon operation, the ambient air via the filter element 10 to the sensor 4.

Figure 11:
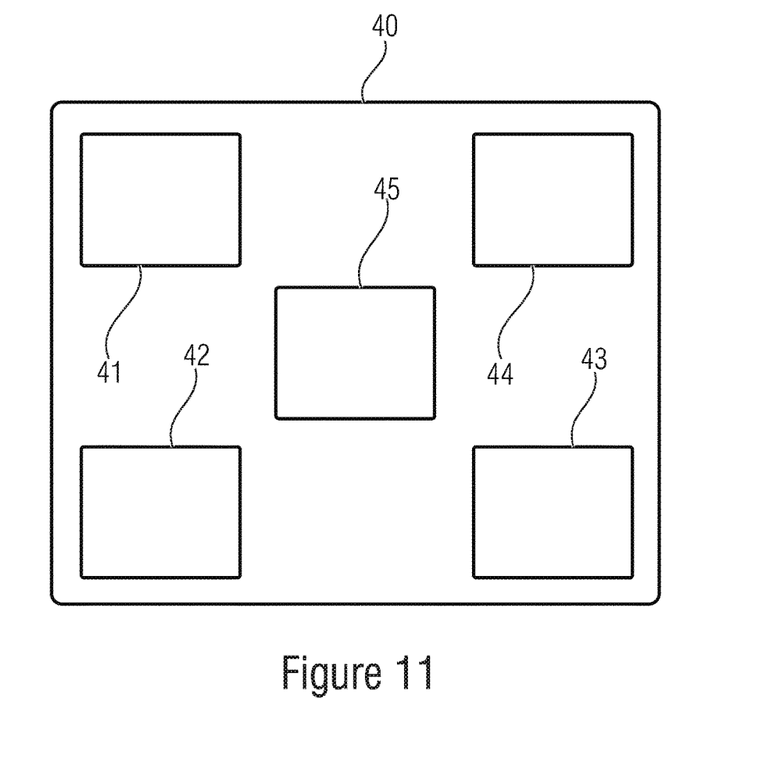
FIG. 11 is a top view of a sensor array.

The sensor 4 shown in FIG. 10 may also be a sensor element, in particular, a sensor array with several sensors. Such a sensor array 40 is shown in FIG. 11.

The sensor array 40 may comprise up to twenty individual sensors. In the embodiment shown in FIG. 11, the sensor element 40 comprises five individual sensors 41, 42, 43, 44, 45, wherein at least one of these sensors is the previously described sensor 4. Each individual sensor 41, 42, 43, 44, 45 may comprise its own fluid channel towards the opening 2.

The individual sensors 41, 42, 43, 44, 45 arranged on the sensor array 40 may be configured to detect the same component in the ambient air. Advantageously, however, the individual sensors 41, 42, 43, 44, 45 are configured to detect different components in the ambient air.

For example, each of the sensors 41, 42, 43, 44, 45 may be configured to sense at least one ambient air component from the group of carbon monoxide CO, carbon dioxide $CO_2$, nitrogen N, dinitrogen monoxide $N_2O$, volatile organic compounds VOC, humidity and fine dust.

After having described the structural features of the apparatus 1 according to the invention, the mode of operation of the apparatus 1 according to the invention will be explained in the following.

The invention is at least partly based on the realization that fluids, and in particular gases, necessitate a certain time for diffusion. Fluids comprise a material-characteristic diffusion coefficient D.

The diffusion coefficient D is a measure of the mobility of the particles in the fluid and may be determined from the average square of the path L traveled per time τ, wherein $$\tau = \frac{L^2}{D}.$$

The diffusion constant D of water vapor in air is 0.24 cm²/s at 24.8° C. [1].

The diffusion of gas in gas, e.g., in the form of moisture in air, is fast on short paths and slow on long paths.

Within the context of the present invention, experiments have been made with a housed sensor 4. The sensor housing comprises an opening to the surroundings. The sensor 4 is arranged within the housing to be spaced apart approx. 500 μm from this opening. For example, the diffusion of the moisture is fast along these 500 μm between the opening and the sensor.

In addition to the opening in the sensor housing, the mobile device 1 itself also comprises an opening 2, as depicted in FIGS. 1 to 3 and 6 to 10. The housed sensor 4 is arranged spaced apart approx. one to two centimeters from the opening 2 provided in the mobile device 1. However, the diffusion of the moisture from the opening 2 provided in the mobile device 1 to the opening provided in the sensor housing was slow on this path with a length L of approx. 1 . . . 2 cm (FIGS. 2 and 3).

Consequently, gas sensors comprising a sensor housing in which its gas inlet opening is spaced apart, e.g., only approx. 500 μm from the sensor membrane, react "quickly" to changes in the ambient air since the diffusion time $t_1$ on this path L is short.

On the other hand, gas sensors being arranged within a mobile device 1 such as a smartphone in which the gas inlet opening 2 is farther away (e.g., 1 . . . 2 cm), i.e., in which the length L between the opening 2 of the mobile device 1 and the sensor 4 is longer (e.g., 1 . . . 2 cm), react "slowly" to changes in the ambient air since the diffusion time $t_2$ on this path L is slower by the factor $(10/0.5)^2=400$, according to the above mentioned law.

In the following, the relative indications "fast" or "slow" are to be specified with numerical values. The tested housed sensor 4 comprised, e.g., a distance with the length L=0.5 mm=0.05 cm between the sensor housing opening and the moisture sensor 4.

As a result:

$$\tau = \frac{L^2}{D} = \frac{0.05^2}{0.25} \text{ s} = 10 \text{ ms}$$

That is, on the short path (0.5 mm) between the sensor 4 and the opening of the sensor housing, the ambient air or rather the moisture contained in the ambient air rapidly diffuses to the sensor 4 and necessitates only approx. 10 ms for travelling this path L.

However, travelling the path between the sensor 4 and the opening 2 provided in the mobile device 1 takes considerably longer. As mentioned at the outset, the tested sensor 4 was arranged spaced apart approx. 1 to 2 cm from the opening 2 of the mobile device 1.

The duration of travelling this path L between the sensor 4 and the opening 2 provided in the mobile device 1 may be calculated by means of the above-mentioned diffusion coefficient D. For example, the ambient air or rather the moisture contained in the ambient air necessitates the following for travelling a path L of 1 cm:

$$\tau = \frac{L^2}{D} = \frac{1}{0.25} \text{ s} = 4 \text{ s}$$

From the above follows that water vapor necessitates only 10 milliseconds for travelling a path L of 0.5 mm, while already 4 seconds are necessitated for travelling a path L of 1 cm.

However, it is to be noted that a moisture molecule only travels this far "on average" during the period of time mentioned. This does not yet mean that the moisture difference is already completely compensated after this period of time. Therefore, a multiple of this time constant has to be awaited until the moisture concentration gradient has completely degraded (which arises, e.g., when pulling the mobile device 1 out of the trouser pocket). A factor of 10 . . . 50 is estimated such that approx. 0.1 . . . 0.5 seconds will be necessitated for the degradation of the moisture concentration gradient in the tested sensor 4 (without being installed in a mobile device 1). However, as soon as this sensor 4 is installed in a mobile device 1, so that the sensor 4 is arranged spaced apart approx. 10 mm from the opening 2 in the mobile device 1 (i.e., diffusion path L of 10 mm), much more time is already necessitated to completely degrade the moisture concentration gradient, i.e., approx. 20 seconds to 5 minutes.

These considerations are supported by the following observations: according to the data sheet, the tested moisture sensor 4 comprises a response time of a few seconds. With the (not installed) sensor 4, these times are also measured. If this sensor 4 is provided with a supply channel 3 of L=10 mm, the response times increase to several minutes.

Likewise, another moisture sensor 4 which has already been installed as a standard feature in a smartphone 1 comprises a response time of several minutes although the sensor 4 "as such" comprises a response time in the range of seconds (approx. 10 seconds).

Other gases of ambient parameters to be measured in mobile electronic devices 1 by gas sensors 4 will have a corresponding slow response time according to their diffusion coefficient. For example, the gases $CO_2$, volatile organic compounds (VOC, such as alcohol), fine dust or toxic gases.

Some examples of gases as components of the ambient air as well as their corresponding diffusion coefficients D at a certain temperature are listed in Table 1 below. [1]

TABLE 1

| Gas in air | Temperature [° C.] | Diffusion coefficient [cm²/s] |
|---|---|---|
| moisture (water) | 24.8 | 0.24 |
| carbon dioxide | 25 | 0.113 |
| ethanol | 25 | 0.135 |
| hydrochloric acid | 21.8 | 0.1246 |
| hydrogen | 27.9 | 0.07 |
| helium | 44 | 0.765 |

The diffusion times according to the above model (l=0.5 mm for sensor housing, L=10 mm for an installation in the mobile device 1) are estimated in the following Table 2:

TABLE 2

| Diffusion gas in air | Temperature [° C.] | Diffusion coefficient [cm$^2$/s] | Diffusion time for I = 0.5 mm [s] | Diffusion time for L = 10 mm [s] |
|---|---|---|---|---|
| moisture (water) | 24.8 | 0.24 | 0.010 | 4.2 |
| carbon dioxide | 25 | 0.113 | 0.022 | 8.8 |
| ethanol (alcohol) | 25 | 0.135 | 0.019 | 7.4 |
| hydrochloric acid | 21.8 | 0.1246 | 0.020 | 8.0 |
| hydrogen | 27.9 | 0.07 | 0.036 | 14.3 |
| helium | 44 | 0.765 | 0.003 | 1.3 |

Consequently, the diffusion times of relevant gases such as carbon dioxide or alcohol are still longer by a factor of approx. 2 as compared to moisture. Thus, these gases comprise an even longer diffusion time compared to the above-mentioned example of water vapor in the ambient air. In the case of larger particles such as fine dust, the diffusion processes take even longer.

By providing a micropump 5, diffusion is at least partially replaced by convection, i.e., the times necessitated for the drawn-in ambient air to reach the sensor 4 may be significantly shortened.

The use of a micropump 5 according to the present invention is also advantageous, amongst other things, since micropumps 5 are small and inexpensive. The other requirements for a micropump 5 (in addition to a small structural size and low production costs) are also easy to fulfill for the application according to the invention:

Only air has to be pumped, i.e., there are no free surfaces or menisci which can interfere with the pumping operation due to their capillary forces
  No forward or counter pressures have to be overcome
  The requirements for the dosing accuracy are not high The advantages of the invention are again summarized in the following. The advantages of a micropump 5 in conjunction with a gas sensor 4 are, among other things:

1. A faster response time since diffusion is replaced by convection
    a. The smallest possible dead volume between intake port 3 and sensor 4
    b. The pump 5 is placed behind the sensor 4 so that the sample does not have to pass through the micropump 5—so that the ambient air may first flow through the sensor 4 unaffected
    c. The sensor 4 does no longer have to be very close to the opening 2 but may be placed further away in the mobile radio device 1
2. The possibility of "resetting" the sensor membrane by removing the desorbed molecules away from the pump 5 after a heating process, which may thus not resorb again on the sensor membrane
    a. Rinsing by overpressure
    b. By applying a strong negative pressure to the membrane 4, however, an additional valve is necessitated in this case
3. The possibility to measure very small concentrations, with preconcentrators
4. The possibility to calibrate the sensor membrane with calibration gases
    a. With a "zero air", e.g., filtered by activated carbon
    b. With additional reservoirs of calibration gases
5. "More defined" passing of the sample to keep the laminated boundary layer small and defined during flowing.

A mobile device 1 according to the invention, in particular in the form of a mobile telephone or smartphone, also comprises the following advantages.

The function of the sensor 4 is as universally and conveniently available as other normal functions of a smartphone 1 (clock, calendar, telephone, SMS, . . . ).
  Modern people have their smartphone 1 at hand.
  The power for pump 5 and sensor 4 may be supplied from the battery of device 1.
  The computing power for evaluating the sensor signal and controlling the pump 5 is provided by the powerful processor.
  By programming an app, every skillful user may graphically represent the sensor signal, automatically carry out repeated measurements, store measured values and share with them other users. Also, a warning function may be programmed.

Further exemplary embodiments of the invention may be embodied, for example, as follows:

A device such as a portable electronic apparatus 1 is conceivable, comprising:
    a micropump 5 comprising an inlet 7 and an outlet 8 for supplying air and its components,
    one (or several) sensor element(s) 4 measuring air parameters, a drawing opening 2 to the surroundings, a fluid line 3 from the suction opening 2 to the sensor element 4,
    wherein the micropump 5 supplies the ambient air so quickly and closely to the sensor element 4 that the sensor element 4 reacts to a change in the air parameter within four seconds.

The ambient air may contain an air component whose air parameters are to be measured.

It is conceivable that the apparatus 1 is further developed in such a way that the sum of the air volume from the drawing opening 2 to the sensor element 4 is less than 200 microliters.

It is conceivable that the apparatus 1 is further developed in such a way that the sum of the air volume from the drawing opening 2 to the sensor element 4 is less than 20 microliters.

Furthermore, a filter 10 may be provided for dust protection, e.g., hydrophobic (water-repellent) filter elements and/or Teflon filters.

The apparatus 1 may also be configured to sense toxic gases in the non-toxic range (e.g., $CO_2$) and/or non-toxic air quality parameters.

The apparatus 1 may comprise sensors without need of regeneration 4.

It would also be conceivable that the sensor chamber is designed to be evacuated for a zero-point definition (for sensors without need of regeneration).

The following exemplary embodiments and further developments of the apparatus 1, e.g., for calibrating the sensor 4 would also be conceivable, e.g., an apparatus according to the invention, comprising:

a filter element 10,
  a second fluid line 13 to the sensor element 4,
  the filter element 10 being accommodated in the second fluid line 13

It is conceivable that the apparatus 1 is further developed in such a way that the filter element 10 is an activated carbon filter.

It is conceivable that the apparatus 1 is further developed so that a second micropump 15 with an inlet and an outlet is provided, the second micropump 15, upon actuation, supplies the ambient air via the filter 10 to the sensor element 4

With the apparatus 1 according to the invention, the following application scenarios would be conceivable:

Monitoring air quality by detecting non-toxic gases or toxic gases in the non-toxic range.

In particular sensors 4 also measuring other phases (liquids, solids) in the air (moisture, fine dust). Use of sensors 4 not requiring a regeneration phase since they do not cause a permanent physical-chemical change at the sensor 4.

Use of evacuation, not to accelerate regeneration, but to enable zero-point calibration (measuring) and adjustment (gauging).

Sensor 4 is only connected to the inlet of pump 5, use of pump 5 at a certain frequency for reverse pumping, therefore no additional need for active valve.

Air flow could be fed back via the sensor 4 in order to cool the sensor element 4 or the regions around the sensor 4, which are heated by the electronic device 1 and may falsify the sensor signal by such a temperature increase.

Further aspects:

regeneration, i.e., heating and pumping away the heated molecules multi-point calibration with calibration gas sensor array 40 negative pressure

Therefore, it is essentially sufficient to direct the sample (ambient air) with a micropump 5 "near" to a (e.g., housed) sensor with its hole, the "last mile" (i.e., the transport path within the sensor housing) then makes the diffusion fast enough.

In this case, "near" is meant in relation to the diffusion lengths L of the air parameter to be measured, taking into account an acceptable reaction time of the gas sensor 4 of a few seconds.

Therefore, a technology is proposed which supplies the analyte to the sensor 4. Micropumps 5 may supply fresh room air to the sensor 4 with a few pump strokes, thus enabling a fast, delay-free and correct measurement signal of the sensors 4.

According to a further embodiment, instead of a single sensor 4, several sensors such as several micro gas sensors 4 for smartphones 1 may be provided, which are supported by a micropump 5. In this regard, reference is made once again to FIGS. 9, 10 and 11. In particular, FIG. 11 shows a sensor array 40 with a plurality of sensors 41, 42, 43, 44, 45.

In this regard, it would be advantageous if, e.g., a micropump 5 was available which supplies a mini-sensor array 40 for several gas and particle measurements in smartphones 1 or other portable devices such as watches, bracelets, tablets, desktops, laptops, household appliances and wall-mounted devices.

As mentioned at the outset, a detection of gases such as $CO$, $N_2O$ or VOC as well as of water contents and the gas composition in our surroundings is in the interest of many people using portable devices 1.

In addition, most people would like to instantly sense air-polluting gases, fine dust and all-genic particles such as pollen at their location with their smartphone 1 or a similar portable device 1 or household device 1, or receive early warnings against allergenic substances and hazardous gases. Moreover, the detection of odors such as breath alcohol, mouth odor and many other odors is of interest.

Sensors are available for many of the applications mentioned. In some cases, they occur in the form of bulky, stand-alone devices. In many cases mouthpieces may be used with these devices, which most people do not like.

Although many of the available sensors (such as humidity, volatile organic compounds, CO or NO) or sensors based on organometallic, optical, or resonance principles comprise form factors and an appropriate cost-effectiveness for the use with smartphones 1, a commercial use is not possible, since the gas, the odor or the fine dust may not be brought quickly and reliably to the sensor in a smartphone in all sensor principles.

However, this is necessitated in order to provide the average user of smartphones 1 with a meaningful and fast measurement result. Reliable data for gas measurements may provide meaningful overviews of gases of the surroundings, e.g., air pollution along roads or in large cities or pollen maps for allergic persons.

Most sensors also necessitate a gas desorption away from the sensor surface for regeneration, which in most cases is achieved by heat. The gases have to be transported away and this process is too slow if it is only driven by diffusion.

An additional problem is that stand-alone devices with sensors necessitate display and calculation capabilities, which incurs additional costs.

An array 40 of sensors 41, 42, 43, 44, 45 (from one sensor to up to twenty sensors) may be used to sense a wide range of gases, odors, or fine particles. The sensor devices themselves are partly available, are under development or will be available in the near future.

A micropump 5 is proposed to supply fresh gases, odors or fine particles to the sensor 4 on the inside of a smartphone 1 in a short period of time (e.g., within a few seconds or faster).

All display functions, the touch panel and the necessitated computing power of smartphones 1 (or similar portable devices 1) are already available at no extra cost. A memory function for viewing the measurement after the smartphone 1 has been exposed to a gas and viewing the result later may be easily integrated.

In addition, new sensor developments may be easily integrated into the concept to keep the device 1 up-to-date.

A micropump 5 also enables a rapid gas desorption away from the sensor surface to allow new gas measurements.

A further problem occurs with sensors requiring high temperature regeneration. In this case, a rapid gas transport away from the sensor region is also a task which is solved by micropumps 5.

A micropump 5 comprising the dimensions $5 \times 5$ mm$^3$ or smaller and a height of <1 mm is proposed in order to pump the gases or fine dust particles to be measured from the outside of a smartphone 1 into the smartphone 1 to a single sensor 4 or advantageously to an array 40 of several gas and/or particle sensors 41, 42, 43, 44, 45.

Sensors 4 comprising a component size of a few square millimeters (e.g., $1.5 \times 1.5$ mm and a height <1 mm) are advantageous for this purpose. This means that they may be arranged next to one another or even stacked under or above a micropump 5. Gas channels 3 may be produced to be small enough but to nevertheless allow sufficient gas throughput so that the gas may be pumped from the outside of the smartphone 1 via all sensors 4, 41, 42, 43, 44, 45. The pump 5 is advantageously arranged below the sensing areas or downstream of the sensor 4 and/or the sensors 41, 42, 43, 44, 45.

In particular, silicon micropump chips 5 with a small form factor are advantageous in order to reduce costs and still maintain the performance in terms of flow rate and counter pressure. Therefore, a concept according to the invention may be, amongst others, to combine and to reduce all parts (pump 5, gas channels 3, 13, sensor array 40 and filter 10, if necessitated) to fit into a smartphone 1 (or similar portable device 1) based on the form factor and the costs.

During the above-mentioned tests of housed moisture sensors 4, amongst others, the following effects could be observed.

On the one hand, a sponge effect occurred in materials of the fluid module.

1. Sponge effect with materials of the fluid module
   a. by materials absorbing moisture (plastics . . . ) in the range of minutes
   b. by adhesion of moisture molecules to surfaces (in the range of seconds)
   C. on rough surfaces: spontaneous condensation in nanospheres On the other hand, a sponging effect was observed in the sensor membrane itself.

2. The sponging effect of the sensor membrane itself
   The sensor membrane itself is a moisture sink that may absorb a certain amount of moisture.

From these findings, the following applies with respect to the fluid module:
   if possible, no absorbing of moisture in all materials, so that no sponge effect occurs
   smoothest possible surfaces where as little moisture as possible may adsorb While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

SOURCES

[1] Taschenbuch für Chemiker and Physiker: *Band* 1: *Makroskopische physikalisch-chemische Eigenschaften*, Ed. 3, E. Lax Nov. 27, 2013, Springer-Verlag

The invention claimed is:

1. A mobile device, comprising:
   an opening defining a fluid connection between a fluid channel in the mobile device and ambient air,
   a sensor arranged in the fluid channel, configured to sense at least one component of the ambient air,
   a micropump configured to draw in ambient air through the opening and to convey the same to the sensor,
   wherein the sensor is arranged spaced apart from the opening, and
   the volume of the fluid channel between the sensor and the opening is less than 20 microliters and the length of the fluid channel between the sensor and the opening is less than 25 mm, advantageously less than 15 mm and more advantageously 10 mm or less,
   wherein the mobile device comprises a filter and a second fluid channel configured to transport the drawn-in ambient air to the sensor, wherein the filter is arranged in the second fluid channel, and
   wherein the mobile device further comprises a second micropump configured to draw in the ambient air and to transport the same to the sensor through the second fluid channel.

2. The mobile device according to claim 1, wherein the mobile device is a mobile telephone and the opening provided in the mobile telephone is a microphone opening.

3. The mobile device according to claim 1, wherein the length of the fluid channel between the sensor and the opening is at least 5 mm.

4. The mobile device according to claim 1, wherein the micropump comprises a lateral dimension of 5×5 mm or less and a height of 1 mm or less.

5. The mobile device according to claim 1, wherein the sensor comprises a lateral dimension of 1.5×1.5 mm or less and a height of 1 mm or less.

6. The mobile device according to claim 1, wherein the mobile device comprises a sensor array comprising at least the one sensor and at least one further sensor for sensing a component of the ambient air, and wherein the sensor array advantageously comprises a total of up to twenty sensors for sensing a component of the ambient air.

7. The mobile device according to claim 1, wherein the micropump is arranged upstream of the sensor.

8. The mobile device according to claim 1, wherein the micropump is arranged downstream of the sensor.

9. The mobile device according to claim 1, wherein the filter comprises an activated carbon filter, a hydrophobic filter, a hydrostatically charged filter or a polytetrafluoroethylene filter.

10. The mobile device according to claim 1, wherein the sensor is configured to sense at least one component from the group comprising carbon monoxide (CO), carbon dioxide ($CO_2$), nitrogen (N), dinitrogen monoxide ($N_2O$), volatile organic compounds (VOC), humidity, allergenic substances and fine dust.

11. The mobile device according to claim 1, wherein the sensor is a sensor without need of regeneration.

12. The mobile device according to claim 1, wherein the mobile device is a bracelet, a watch, a tablet or a notebook.

* * * * *